US006168918B1

(12) United States Patent
Satishchandran et al.

(10) Patent No.: US 6,168,918 B1
(45) Date of Patent: *Jan. 2, 2001

(54) METHOD OF DETECTING FOREIGN DNA INTEGRATED IN EUKARYOTIC CHROMOSOMES

(75) Inventors: C. Satishchandran, Lansdale; Richard Benjamin Ciccarelli, Pottstown; Catherine Julia Pachuk, North Wales, all of PA (US)

(73) Assignee: American Home Products Corp., Madison, NJ (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/594,141

(22) Filed: Jan. 31, 1996

(51) Int. Cl.[7] .............................. C12Q 1/68; C12P 19/34; C07H 21/02
(52) U.S. Cl. ...................... 435/6; 435/912; 435/172.3; 435/240.2; 536/23.1
(58) Field of Search .................. 435/6, 91.2, 172.3, 435/240.2; 935/24, 70, 77, 78; 536/23.1

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,945,050 | 7/1990 | Sanford et al. | 435/172.1 |
| 4,960,707 | 10/1990 | Lacks | 435/320 |
| 4,965,188 | 10/1990 | Mullis et al. | 435/6 |
| 5,055,393 | * 10/1991 | Kwoh et al. | 435/6 |
| 5,075,216 | 12/1991 | Innis et al. | 435/6 |
| 5,773,257 | * 6/1998 | Nielson et al. | 435/91.1 |

FOREIGN PATENT DOCUMENTS

| | | |
|---|---|---|
| WO 90/11092 | 10/1990 | (WO). |
| WO/92/22647 | * 12/1992 | (WO). |
| WO 94/16737 | 8/1994 | (WO). |

OTHER PUBLICATIONS

Geier, G. and Modrich, "Recognition Sequence of the dam Methylase of *Escherichia coli* K12 and Mode of Cleavage of Dpn I Endonuclease", *The J. of Biol. Chem.* 1979, 254(4), 1408–1413.

Hsieh, C. et al., "V(D)J Recombination: Evidence that a Replicative Mechanism is Not Required", *Molecular and Cellular Biology* 1991, 11(8), 3972–3977.

Lacks, S. and Greenberg, "Complementary Specificity of Restriction Endonucleases of *Diplococcus pneumoniae* with Respect to DNA Methylation", *J. Mol. Biol.* 1977, 114, 153–168.

Lacks, S. and Greenberg, "A Deoxyribonuclease of *Diplococcus pneumoniae* Specific for Methylated DNA", *The J. of Biological Chem.* 1975, 250 (11), 4060–4066.

Ni, T. et al., "In Vitro Replication of Adeno–Associated Virus DNA", *J. of Virology* 1994, 68 (2), 1128–1138.

Skerra. Nucl. Acids Res. 20:3551–3554, Jul. 1992.*

Herrmann et al. In Meth. Enzymol: Guide to Molecular Cloning Techniques. Academic Press, New York, 152:180–181, 1987.*

Innis et al., editors PCR Protocols. Academic Press, New York (1990) pp. 1–12.*

M.J. Cooper et. al. Biotechniques 16(1):20,22,24 (1994).*

J.B. Findlay et.al. Clinical Chemistry 39(9):1927–1933 (1993).*

A.C. Brewer et al Methods in Molecular Biology vol. 7: Gene Transfer and Expression Protocols p. 405–410 (199 ).*

Sambrook et.al. editors of Molecular Cloning: A Laboratory Manual (1989) Cold Spring Harbor Laboratory Press p. E.34–36.*

Promega Protocols and Applications Guide 1991 p. 22, 41.*

Sigma Molecular Biology Catalog 1996/7 p. 114.*

C. Cousens et.al. Molecular Reproduction and Development 39:384–391 (1994).*

W. Nichols et.al. Annals of N.Y. Acad. Sci 772:30–38 Nov. 27, 1995.*

* cited by examiner

*Primary Examiner*—Jeffrey Fredman
(74) *Attorney, Agent, or Firm*—Howson and Howson

(57) ABSTRACT

Methods of detecting the presence of a plasmid DNA sequence integrated in a chromosomal DNA molecule of a eukaryotic cell in a sample that contains chromosomal DNA molecules of eukaryotic cells and free plasmid DNA molecules are disclosed. According to the invention, chromosomal DNA of eukaryotic cells which are free of deoxyadenosine methyltransferase, and free plasmid DNA molecules which are produced in cells that contain deoxyadenosine methyltransferase and which have a DpnI site, are digested with one or more restriction enzymes that cleave plasmid DNA sequences integrated in the chromosomal DNA and plasmid DNA molecules to produce DNA digestion segments that are then fractionated to produce a plurality of fractions. The DNA digestion segments in each fraction is digested with DpnI and plasmid DNA sequences are amplified using sets of primers that flank a DpnI site in the plasmid DNA sequence. The presence of amplified fragments indicates the presence of a plasmid DNA sequence integrated into the chromosomal DNA.

49 Claims, 1 Drawing Sheet

METHOD OF DETECTING FOREIGN DNA INTEGRATED IN EUKARYOTIC CHROMOSOMES

FIELD OF THE INVENTION

The present invention relates to a method of detecting the presence of stably integrated plasmid DNA sequences in eukaryotic chromosomal DNA in samples that contain a mixture of integrated and free (non-integrated) plasmid DNA molecules.

BACKGROUND OF THE INVENTION

The fields of gene therapy and genetic vaccination include protocols in which nucleic acid molecules, including plasmid DNA molecules and viral genomes, are used as an active agent. The nucleic acid molecules encode proteins that have therapeutic and/or prophylactic effects on the individuals to whom the nucleic acid molecules are delivered. For example, PCT/US94/00899, which is incorporated herein by reference, and the U.S. parent applications to which it claims priority, which are also each incorporated herein by reference, disclose genetic immunization protocols using plasmid DNA delivered in conjunction with compounds that facilitate DNA uptake. PCT/US90/01515, which is incorporated herein by reference describes delivery of naked plasmid DNA, i.e. DNA that is free from any agents which facilitate uptake. Others teach the use of liposome mediated DNA transfer, DNA delivery using microprojectiles (U.S. Pat. No. 4,945,050 issued Jul. 31, 1990 to Sanford et al., which is incorporated herein by reference), and DNA delivery using electroporation. In each case, the DNA may be plasmid DNA that is produced in bacteria, isolated and administered to the animal to be treated. The plasmid DNA molecules are taken up by the cells of the animal where the sequences that encode the protein of interest are expressed. The protein thus produced provides a therapeutic or prophylactic effect on the animal. The use of viral vectors and other means of delivering nucleic acid molecules to cells of an individual in order to produce a therapeutic and/or prophylactic immunological effect on the individual are similarly well known.

Gene therapy and genetic immunization involve the transfer of DNA into cells and the nuclear compartment of cells in vivo. Some forms of gene therapy and DNA vaccination rely on well known methods to insert (integrate) the plasmid DNA into a eukaryotic chromosome. This is carried out to enhance the amount and longevity of DNA expression. Alternatively, DNA might be transferred in a form which does not intentionally integrate, but instead express as an episomal element. This is preferred in genetic immunization procedures, due to the possible consequence or an uncontrolled integration event.

In particular, there is a risk that the transferred DNA will integrate into the chromosome of the eukaryotic cell at a site in the chromosome which results in the cell displaying an abnormal phenotype. Translocations and integration of foreign DNA have been observed in many transformed cells. The observation that integration of foreign DNA into chromosomal DNA can lead to a transformed phenotype is a major concern in protocols which use foreign DNA as an active agent to be delivered to cells. In protocols in which plasmid DNA is used as an active agent, the possibility of plasmid DNA integration into chromosomal DNA presents a potential risk which must be assessed.

There is a need for a highly sensitive and specific assay which can reliably detect the presence of stably integrated DNA sequences in eukaryotic chromosomal DNA in samples which also contain the same DNA sequences in an episomal form which is non-integrated. There is a need for a highly sensitive and specific assay which can reliably detect the presence of stably integrated plasmid DNA sequences in eukaryotic chromosomal DNA in samples which also contain the same plasmid DNA sequences in a form which is non-integrated. There is a need for a highly sensitive and specific assay which can reliably detect the presence of stably integrated viral DNA sequences in eukaryotic chromosomal DNA in samples which also contain the same viral DNA sequences in an episomal form which is non-integrated.

SUMMARY OF THE INVENTION

The present invention provides a method to test whether or not foreign DNA, i.e. plasmid DNA or viral genomic nucleic acid molecules, that is introduced into eukaryotic cells integrates into the chromosomal DNA of the eukaryotic cells. The method provides a simple and efficient means for the identification of integrated foreign DNA sequences in samples which also contain free (non-integrated) foreign DNA molecules. The present invention relates to methods of detecting the presence of foreign DNA that is integrated into eukaryotic chromosomal DNA in a sample that contains free foreign DNA molecules and chromosomal DNA molecules from eukaryotic cells.

According to the invention, the foreign DNA must have certain characteristics. The foreign DNA which can be detected in the method of the invention has at least one DpnI restriction enzyme site as well as one or more non-DpnI restriction enzyme sites which can be cut by non-DpnI restriction enzymes. The foreign DNA molecules must be produced in a cell that has the enzyme deoxyadenosine methyltransferase (dam) so that the foreign DNA has the methylation pattern that is associated with DNA produced in dam$^+$ cells.

According to the invention, the eukaryotic cells into which the free foreign DNA molecules are introduced must not have the enzyme dam so that chromosomal DNA does not have the methylation pattern that is associated with DNA produced in dam$^+$ cells.

The method of the invention comprises a series of steps. The total DNA from eukaryotic cells that contain plasmid DNA is digested with one or more of the non-DpnI restriction enzymes that can cleave the foreign DNA to produce DNA digestion segments of multiple sizes. The DNA digestion segments are then fractionated to produce a plurality of fractions of DNA digestion segments. Fractionation results in the separation of foreign DNA sequences which were integrated from the bulk of the remainder of the chromosomal DNA. In addition, free foreign DNA sequences are also fractionated in a similar manner. The DNA digestion segments in each fraction are then digested with restriction enzyme DpnI. Following DpnI digestion, fragments of foreign DNA are amplified using sets of primers that flank a DpnI restriction enzyme site in the foreign DNA. Free, non-integrated foreign and native chromosomal DNA sequences are not amplified. Detection of the presence of amplified fragments indicates that foreign DNA has integrated into eukaryotic chromosomal DNA.

Some preferred embodiments of the present invention provides a method to test whether or not plasmid DNA that is introduced into eukaryotic cells integrates into the chromosomal DNA of the eukaryotic cells. The method provides a simple and efficient means for the identification of integrated plasmid DNA sequences in samples which also contain free (non-integrated) plasmid DNA molecules. Some preferred embodiments of the present invention relates to methods of detecting the presence of plasmid DNA that is integrated into eukaryotic chromosomal DNA in a sample that contains free plasmid DNA molecules and chromosomal DNA molecules from eukaryotic cells.

According to the invention, plasmid DNA must have certain characteristics. The plasmid DNA which can be detected in the method of the invention has at least one DpnI restriction enzyme site as well as one or more non-DpnI restriction enzyme sites which can be cut by non-DpnI restriction enzymes. The plasmid DNA molecules must be produced in a cell that has the enzyme deoxyadenosine methyltransferase (dam) so that the plasmid DNA has the methylation pattern that is associated with DNA produced in dam+ cells.

According to some of the preferred embodiments of the invention, the eukaryotic cells into which the free plasmid DNA molecules are introduced must not have the enzyme dam so that chromosomal DNA does not have the methylation pattern that is associated with DNA produced in dam+ cells.

Some of the preferred embodiments of the method of the invention comprises a series of steps. The total DNA from eukaryotic cells that contain plasmid DNA is digested with one or more of the non-DpnI restriction enzymes that can cleave the plasmid DNA to produce DNA digestion segments of multiple sizes. The DNA digestion segments are then fractionated to produce a plurality of fractions of DNA digestion segments. Fractionation results in the separation of plasmid DNA sequences which were integrated from the bulk of the remainder of the chromosomal DNA. In addition, free plasmid DNA sequences are also fractionated in a similar manner. The DNA digestion segments in each fraction are then digested with restriction enzyme DpnI. Following DpnI digestion, fragments of plasmid DNA are amplified using sets of primers that flank a DpnI restriction enzyme site in the plasmid DNA. Free, non-integrated plasmid and native chromosomal DNA sequences are not amplified. Detection of the presence of amplified fragments indicates that plasmid DNA has integrated into eukaryotic chromosomal DNA.

DETAILED DESCRIPTION OF THE INVENTION

Figure 1:
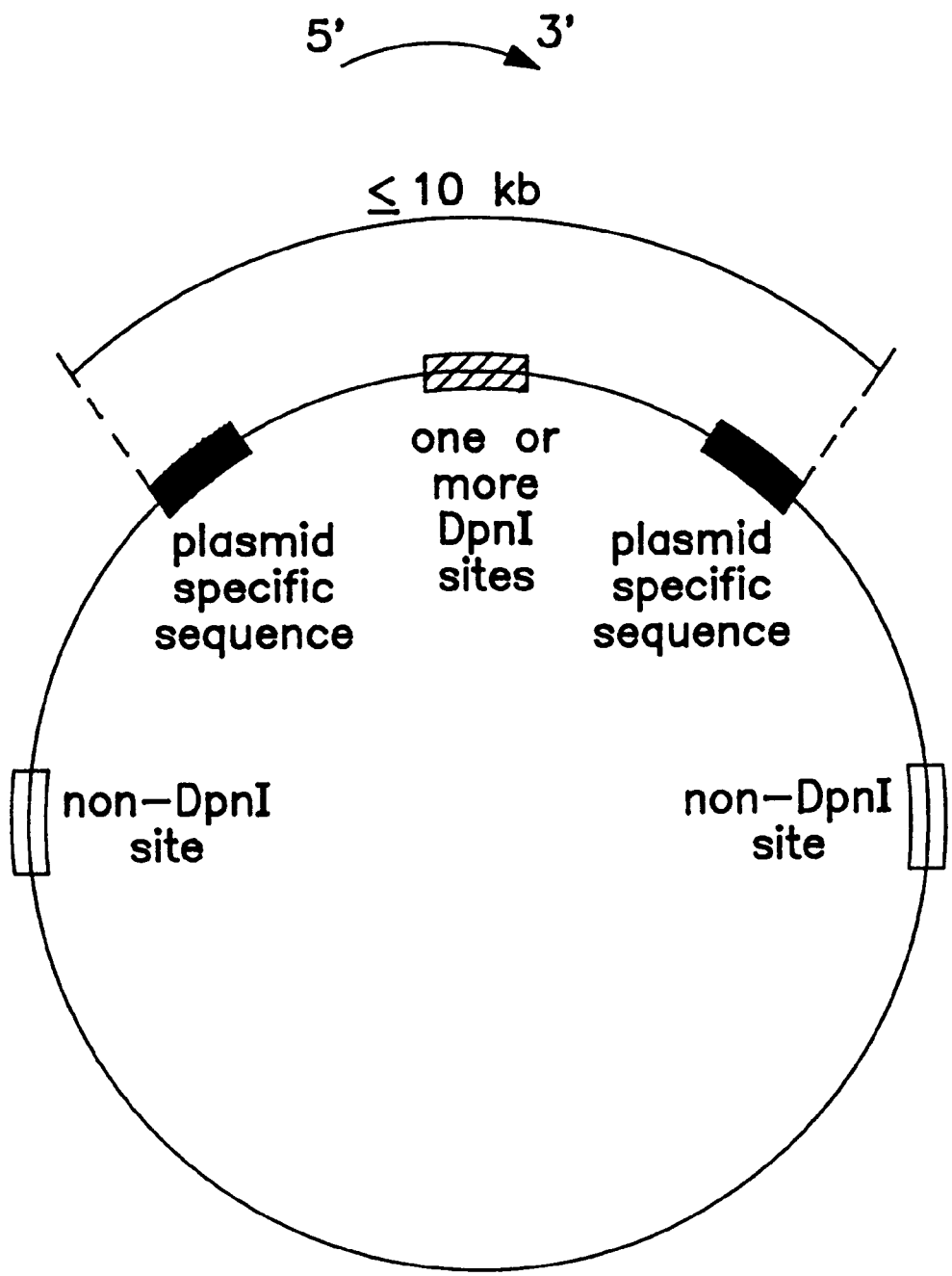
FIG. 1 is a diagram of the relative locations of restriction sites and primer-hybridization sequences the foreign DNA. DNA having these characteristics may be a plasmid or the genome of a foreign vector.

The present invention relates to methods of detecting whether or not foreign DNA that is introduced into eukaryotic cells integrates into the chromosomal DNA of the eukaryotic cells. As used herein, the term "foreign DNA" is meant to refer to plasmid DNA or viral genomic nucleic acid molecules. In some preferred embodiments of the invention, the foreign DNA is plasmid DNA. It is contemplated that the present invention can be employed using viral genomic DNA in place of plasmid DNA. Accordingly, the methods and materials described herein as referring to plasmids are intended to also include methods and materials in which the plasmid DNA may be substituted with viral genomic nucleic acid molecules. It is contemplated that references to plasmids in methods and materials includes methods and materials using plasmid DNA sequences or viral genomic nucleic acid sequences.

As used herein, "dam" is meant to refer to the enzyme deoxyadenosine methyl transferase. The enzyme dam methylates the adenine when it occurs in the nucleotide sequence GATC.

As used herein, "dam+ cells" is meant to refer to cells that produce dam. Certain bacterial strains such as *E. coli* K12 strains produce dam naturally. Bacterial strains as well as eukaryotic host cells such as yeast, insect cells, mammalian cells, plant cells, etc. may also be transformed with an expression vector that encodes dam and such cells are converted into dam+ cells. DNA that contains the sequence GATC and that is produced in dam+ cells will have the adenine in the GATC sequence methylated.

As used herein, the term "free plasmid DNA molecules" is meant to refer to plasmid DNA molecules which are not integrated into the chromosome of a eukaryotic cell.

As used herein, "dam− cells" is meant to refer to cells which do not have dam. Unless transformed within heterologous dam gene, eukaryotic cells do not contain dam and are therefore dam− cells. DNA that contains the sequence GATC that is produced or repaired in dam− cells will not have the adenine methylated.

As used herein, the term "integrated plasmid DNA sequences" is meant to refer to plasmid DNA which has integrated into the chromosome of a eukaryotic cell.

As used herein, the term "plasmid-specific DNA sequences" is meant to refer to nucleotide sequences which are known to be present in plasmid DNA molecules. Plasmid-specific DNA sequences are preferably not found in eukaryotic chromosome DNA in the absence of integrated plasmid DNA.

As used herein, the term "plasmid-specific primers" is meant to refer to primers that hybridize to plasmid-specific DNA. Plasmid-specific primers will not amplify DNA sequences found in eukaryotic chromosomal DNA in the absence of integrated plasmid.

As used herein, the term "sets of primers that flank the DpnI site" is meant to refer to sets of primers that hybridize to a nucleic acid molecule at nucleotide sequences relative to each other on either side of a DpnI restriction site. Accordingly, if the nucleic acid molecule is intact, the primers can be used to amplify by PCR the sequences of the nucleic acid molecule between the primers including the nucleotides that make up the DpnI site but if the nucleic acid molecule is digested with DpnI, the primers cannot amplify the sequence between them. It is possible that some of the primer sequences overlap the DpnI site or sites. However, it is preferred that the primer sequences flank the DpnI site or sites.

As used herein, "non-DpnI restriction enzymes" are those which can cut DNA at a specific site regardless of whether or not the nucleotide site is methylated to display a dam+ methylated pattern.

DpnI is a restriction enzyme described in U.S. Pat. No. 4,960,707 issued Oct. 2, 1990 to Lacks, which is incorporated herein by reference. It is known that the restriction enzyme DpnI recognizes and cleaves nucleic acid molecules at the nucleotide sequence GATC if the adenine is methylated. DpnI will not recognize and cleave nucleic acid molecules at the nucleotide sequence GATC if the adenine is not methylated.

The present invention provides an integration assay which is useful to detect whether or not plasmid DNA that is taken up by eukaryotic cells integrates into the chromosomal DNA of the eukaryotic cells. Accordingly, the present invention provides a means to detect integration of plasmid DNA useful as agents in gene therapy and/or genetic immunization protocols. The present invention is thereby useful as a means to address safety concerns and issues associated with such protocols.

The invention relates to a PCR method which utilizes the selective digestion of certain DNA molecules by DpnI. DpnI will only digest DNA having a specific sequence and methylation pattern. The endonuclease DpnI digests potential "contaminant" free plasmid DNA molecules before the PCR reaction is carried out. The DpnI restriction endonuclease recognizes and cleaves GATC sequences that are methylated at the adenine residue, but does not cleave unmethylated GATC sequences. Since DpnI will only cleave DNA molecules at the GATC sequence if the adenine is methylated, DpnI will cleave plasmid DNA molecules that have the sequence GATC if the plasmid DNA is produced in dam$^+$ cells. DpnI will not cleave eukaryotic chromosomal DNA molecules if the eukaryotic cells are dam$^-$. Furthermore, DpnI will not cleave plasmid DNA integrated into eukaryotic chromosomal DNA if the integrated plasmid DNA has been repaired or reproduced in the eukaryotic cell. Plasmid DNA that has been integrated into eukaryotic chromosomal DNA (or any other dam$^-$ cell) and which has undergone subsequent repair and/or replication, will acquire the unmethylated GATC pattern.

The method is especially useful in an integration assay. It permits the detection of integrated plasmid sequences in the presence of the same free plasmid DNA molecules. Plasmid or other vector DNA molecules that has been produced in a dam$^+$ host cell will have methylated GATC sequences and will be cleaved by DpnI; plasmid sequences that have been integrated into mammalian chromosomal DNA (or the DNA of any dam$^-$ cell), and which have undergone subsequent repair and/or replication, will acquire the unmethylated mammalian GATC pattern. Accordingly, digestion with DpnI will result in selective cleavage of free plasmid DNA molecules in the presence of mammalian genomic DNA which might contain integrated plasmid sequences.

The eukaryotic cells used in the invention are dam$^-$ that their chromosomal DNA molecules do not have the characteristic methylation pattern associated with dam$^+$ cells. That is, in each instance in which the chromosomal DNA molecule of a dam_ cell has the sequence GATC, the adenine is not methylated. Therefore, the chromosomal DNA molecule of a dam_ cell will not be cut by DpnI at that site. In preferred embodiments, the eukaryotic cells that are used are from test animals which have been administered plasmid DNA molecules. In some embodiments, animals are administered plasmid DNA and total DNA is extracted from samples of cells and/or tissue at and/or near the site where the plasmid DNA was administered. In some embodiments, the animal is a mammal such as a monkey, a dog, a rabbit or a rodent, particularly a rat or mouse. In some embodiments, the animal is a human or non-human primate.

The plasmid DNA molecules used in the invention are produced in dam$^+$ cells. Accordingly, in each instance in which the plasmid DNA molecule has the sequence GATC, the adenine is methylated. In some preferred embodiments, the dam$^+$ cells are dam$^+$ bacterial cells. In some preferred embodiments, the dam$^+$ cells are dam$^+$ *E. coli* cells. In some preferred embodiments, the dam$^+$ cells are dam$^+$ *E. coli* K12 strains, e.g., DH10B, W3110, EMG2, and DH5α. Although the dam enzyme occurs naturally in a number of bacteria, especially *E. coli* K12 strains, dam can be cloned into bacteria, yeast, plants, insect cells or even mammalian cells, so that the described integration assay can be utilized using vector DNA molecules produced in such dam$^+$ systems. Alternatively, the plasmid can be methylated using isolated dam enzyme in vitro.

According to the invention, plasmid DNA molecules are provided which contain specific known restriction enzyme cleavage sites and sequences that hybridize to amplification primers, i.e. plasmid-specific primers. The restriction enzyme cleavage sites include at least one DpnI site as well as two or more non-DpnI restriction enzyme cleavage sites that are cut by restriction enzymes without regard to dam-mediated methylation patterns. The plasmid DNA molecules include sequences that flank at least one DpnI restriction site, preferably two or more DpnI restriction sites, more preferably three or more DpnI restriction sites. The sequences are present on both sides of the DpnI site(s) in order to hybridize with plasmid-specific primers and be amplified as part of plasmid sequence fragments if the molecule is not cleaved by DpnI. Amplification will not occur if the molecule is cleaved by DpnI. The at least two non-DpnI restriction enzyme cleavage sites are not within the primer sequences nor are they within the sequence between primers which is amplified.

The non-DpnI restriction enzymes are those which can cut DNA at its specific site regardless of whether or not the DNA molecule has the a dam$^+$ methylation pattern. It is preferred that the plasmid DNA sequence contains a high ratio or frequency of sites for cleavage by the non-DpnI restriction enzyme or enzyme compared to the chromosomal DNA. By cleaving the plasmid DNA at at least two non-DpnI restriction enzyme cleavage sites that are not within the primer sequences nor are they within the sequence between primers which is amplified, the digestion with such enzyme(s) generates a linear fragment which includes the primer sequences and the sequence between primers. By cleaving the plasmid DNA relatively more times than the chromosomal DNA, more of the smaller DNA digestion segments produced by the digestion using non-DpnI restriction enzyme are fragments of plasmid DNA sequences. Accordingly, in some preferred embodiments, non-DpnI restriction enzymes are selected which are known to digest eukaryotic chromosomal DNA infrequently. Restriction enzyme sites cut by such non-DpnI restriction enzymes are included in plasmid DNA sequences. Preferably, to achieve higher sensitivity, restriction enzyme(s) are chosen so there will be 1) more than two cut sites in the plasmid, and, preferably, 2) increased frequency of plasmid cutting relative to chromosomal DNA. In some preferred embodiments, plasmid DNA sequences include a combination of Nru1 and Sac1 sites.

Plasmids are usually about 500 bp–150 kb total, most often 5–7 kb. The relative locations of restriction sites and plasmid specific sequences are described in FIG. 1. Although depicted as a single DpnI site, more than one DpnI site may be 3, 4, 5 included between the plasmid specific sequences. It is also contemplated that the one or more DpnI sites overlap with one or both plasmid specific sequences. The plasmid specific sequences are adjacent on either side of the one or more DpnI sites: one of the plasmid specific sequences is upstream of the DpnI site(s) and the other is downstream. The plasmid specific sequences may be separated from the DpnI site(s) by up to 10 kb. However, the total number of sequences that the plasmid specific sequences may be separated from each other is up to 10 kb, the upper limit of PCR. In some embodiments, the total number of sequences that the plasmid specific sequences may be separated from each other is 200 bp–5 kb. It is preferred that the plasmid specific sequences are each about 1000 basepairs from the DpnI site(s). The plasmid has at least two non-DpnI sites: one non-DpnI site is upstream of the plasmid specific sequences that is upstream of the DpnI site(s) and the other is downstream of the plasmid specific sequences that is downstream of the DpnI site(s). The plasmid specific sequences do not contain the non-DpnI sites used. When the plasmid is cut using the non-DpnI restriction enzyme, a fragment is produced which includes the DpnI site(s) and plasmid specific sequences. It is preferred that this fragment is about 100 bp–8 kb, more preferably 2 kb–5 kb.

The integration assay of the invention can, in the presence of free plasmid DNA molecules that are produced in $dam^+$ cells, detect the presence of any plasmid DNA sequences that have integrated into the chromosomes of a $dam^-$ eukaryotic cell and that have subsequently undergone repair and/or replication. According to the invention, free plasmid DNA molecules that are introduced into eukaryotic cells, such as the cell of an animal being treated with the plasmid DNA molecules as active ingredients of in gene therapy and/or genetic immunization protocols, remain susceptible to digestion by DpnI. However, if the plasmid DNA molecule integrates into the chromosomal DNA molecule of the eukaryotic cell and subsequently undergoes repair and/or replication, it will no longer have the methylation pattern associated with plasmid DNA produced in $dam^-$ cells. Thus, it will not be digested by DpnI.

Cell/tissue samples are obtained by routine methods such as scraping, surgical removal of a sample, or aspiration by syringe or canula. Total DNA from samples of eukaryotic cells that have been exposed to plasmid DNA molecules is subjected to series of steps to determine if any of the plasmid DNA molecules have integrated into the eukaryotic chromosomal DNA molecule. The steps include: digestion using one or more non-selective restriction enzymes; fractionation of the digested DNA; DpnI digestion of the fractionated material; amplification of plasmid sequences using primers which amplify fragments that have an internal DpnI site; and detection of amplified fragments. According to the present invention, the ability of DpnI to selectively cleave methylated sequences but not unmethylated sequences, coupled with the ability to specifically amplify nucleotide sequences even if present in single copy amounts, provides the means to detect plasmid DNA integrated into eukaryotic chromosomes in samples which contain free plasmid DNA even if only a single copy of plasmid DNA has integrated.

A sample of DNA which includes free plasmid DNA and eukaryotic chromosomal DNA, which may or may not contain integrated plasmid DNA sequences, is digested with one or more restriction enzymes which cleave DNA molecules regardless of the methylation pattern. Thus, the restriction enzyme(s) is not DpnI. Digestion of the DNA with the non-DpnI, non-selective/methylation sensitive restriction enzyme(s) produces DNA digestion segments. It has been discovered that in order to achieve the necessary sensitivity to identify integrated plasmid DNA sequence in samples that contain free plasmid DNA molecules, the total isolated DNA which contains free plasmid DNA, mammalian chromosomal DNA, and possibly, chromosomal DNA with integrated plasmid sequences is cut with one, or preferably two or more different non-DpnI restriction enzymes. The restriction enzymes used are preferably chosen so as to cut the chromosome infrequently, but to cut the plasmid frequently. Since the plasmid is a known entity, one or more sequence-specific restriction endonucleases can be selected, which will cleave at least once within the vector, but will make relatively few cuts within the chromosomal DNA. Use of one or more restriction enzymes that cut the chromosome infrequently will result in predominantly large chromosomal fragments, so that a decreased content of genomic sequences can be achieved in those fractions containing smaller fragments that contain plasmid sequences. This results in a higher sensitivity for integrated plasmid sequences when DNA fractions are analyzed. In some embodiments, a combination of Nru1 and Sac1, both of which are 6-cutters, are used together. In some embodiments, plasmids contain a total of five sites cut by this combination. In some embodiments, an eight base cutter, Not1, is used, which cuts at more than one site. Any number of combinations of one or more sequence-specific restriction endonucleases could be selected to achieve similar results. Preferably, such enzyme(s) will cut the plasmid more than once as well as having a quarter frequency of cutting the plasmid relative to the chromosomal DNA. Any restriction enzyme that cleaves DNA molecules regardless of dam-mediated methylation patterns may be used. The plasmid has preferably more than one restriction site susceptible to cleavage by this/these enzyme(s) but not within or between the sequences complementary to amplification primers that flank the DpnI site. Examples of such non-DpnI restriction enzyme sites include NruI, SacI, Not1, Pac1, St1, Smu1, Sal1, etc.

Following digestion, the DNA digestion segments are fractionated to produce a plurality of fractions of DNA digestion segments. The DNA is physically fractionated using any of a variety of known methods, e.g., gel filtration which fractionates on the basis of size, capillary electrophoresis which fractionates on the basis of charge, gel electrophoresis which fractionates on the basis of size and charge, anion exchange chromatography which fractionates on the basis of negative charges, reverse phase chromatography which fractionates on the basis of hydrophobicity and ion pair chromatography which fractionates on the basis of charge and hydrophobicity, or sucrose or other gradient methods which fractionate on the basis of density. In a preferred embodiment, the DNA digestion segments are fractionated by a gel filtration column chromatographic method, using, e.g., Sephacryl™ S1000. The physical fractionation separates the various DNA fragments into a range of sizes. The gel filtration method results in an elution distribution wherein the large fragments come off first whereas the smaller fragments are held up longer and come off the column later. The large chromosomal fragments (~100 kb) elute first, there is a peak of mid-size fragments (~30–40 kb), and the small plasmid fragments, from both free plasmid DNA molecules and potentially integrated plasmid DNA sequences (~2 kb or less), are eluted last. These fragment sizes will of course vary depending on the known plasmid sequence, the host genome, and the number and nature of the restriction enzymes selected. DNA digestion segments may be fractionated by any of several well known fractionation criteria such as size, charge, size and charge, hydrophobicity and density using well known and routine methods. Size fractionation may be done by size exclusion chromatography. Charge fractionation may be done by capillary electrophoresis. Size and charge fractionation may be done by agarose gel electrophoresis.

To eliminate the DNA digestion segments produced by digestion of free plasmid DNA molecules, each fraction is digested with DpnI before carrying out PCR. The DpnI digests all DNA that exhibits $dam^+$ methylation at the sequence GATC but will not digest the GATC sequence with an unmethylated adenine. Thus, free plasmid DNA will be digested at a site within the sequence between the sequences to which the plasmid-specific primers hybridize. DpnI digestion is done under optimal conditions in PCR buffer which has been modified to contain 5 mM DTT protocols using manufacturers instructions.

Following DpnI digestion, fragments of DNA are amplified with plasmid-specific primers which flank DpnI sites. Only uncut DNA will yield amplification products. Thus, only fragments of integrated plasmid DNA which has undergone repair or replication will be amplified. DNA replication and/or DNA repair following integration converts the integrated sequence to a mammalian pattern. The adenine of GATC is no longer methylated. DpnI will no longer cut it, and it will be amplified by PCR. Primer sequences are selected based upon their being adjacent to a DpnI site in the plasmid DNA sequence. Primers can be 10–200 nucleotides in length, more preferably 30 nucleotides in length to amplify a sequence of 20–200 nucleotides which includes a DpnI site between the sequences that hybridize to the primers. The sequence between the primers will preferably contain more than one DpnI site, more preferably, three or more DpnI sites. A plurality of DpnI sites is preferable because some GATC sites in the plasmid may escape methylation even in dam$^+$ bacteria. Sensitive PCR can be achieved with DNA segments of 10 Kb or even greater, but it is preferable that the segment to be amplified is less than 1 Kb. Even smaller segments (e.g., 100 bases), can be amplified, but with smaller segments, methods for detection of amplified fragments might have to be modified, e.g., use of a higher gel, OT HPLC or by incorporation of radiolabelled into product. Amplification is done following standard protocols using manufacturers instructions. In some preferred embodiments, sets of primers amplify fragments, which include at least one DpnI site between primer sequences, of up to 10000 nucleotides. In some preferred embodiments, sets of primers amplify fragments 25–5000 nucleotides. In some preferred embodiments, sets of primers amplify fragments 1000–2000 nucleotides. In some preferred embodiments, sets of primers amplify fragments 500–1500 nucleotides. In some preferred embodiments, sets of primers amplify fragments 1000–4000 nucleotides. In some preferred embodiments, sets of primers amplify fragments about 100–500 nucleotides.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENE AMP RNA PCR kit, Part No. N808-0017.

Some simple rules aid in the design of efficient primers. Typical primers are 18–28 nucleotides in length usually having 50% to 60% g+c composition. The entire primer is preferably complementary to the sequence it must hybridize to. Preferably, primers generate PCR products 100 basepairs to 2000 base pairs, in length. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which forms complementary strands of the nucleotide sequence extending from and between the site where the primers hybridize to the nucleotide sequence. The primers hybridize to the primer extension fragments so produced and, together with the enzyme and free nucleotides, produce additional primer extension fragments. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

Detection of an amplification product of the size of the plasmid fragment amplified by the plasmid specific primers indicates plasmid DNA integration. Amplified DNA may be detected by well known methods such as, for example, by gel electrophoresis. In some embodiments, the PCR reaction sample is run on an agarose electrophoresis gel with a DNA fragment the size of the expected amplified DNA in an adjacent lane to serve as a control. The expected size of the DNA fragment is known from the plasmid sequence. If a DNA sequence is amplified using the plasmid-specific primers in a PCR reaction, the DNA molecule will run in the gel the same distance as the control, indicating integration of plasmid sequences in chromosomal DNA molecules. If integration is detected, its identity can be confirmed using a plasmid-specific probe, which can be the plasmid itself or an oligonucleotide probe at least 15 bases in length.

In preferred embodiments, the DpnI digestion and the PCR are carried out in a closed system so that no contamination can occur after the DpnI digestion. The DpnI PCR methodology involves the addition of DpnI to the PCR tubes. The PCR tubes are sealed and predigestion with DpnI at 27–42° C., preferably 37° C., is carried out before the usual PCR cycles, preferably using multiple primer sets designed to detect known plasmid sequences with the required specificity. The PCR primers are chosen to flank the DpnI sites on the plasmid, so that the cleaved free plasmid will not be amplified. Integrated plasmid sequences, on the other hand, will not be cleaved by DpnI and will be amplified. The closed-system DpnI digestion, followed by PCR, not only eliminates free plasmid from genomic DNA tissue preparations, it eliminates "false positives" due to "airborne" control DNA contamination. The closed-system DpnI PCR method is expected to be generally useful in PCR methods for elimination of airborne bacterial DNA contamination.

Some preferred embodiments of the invention relate to specific reaction conditions, buffers, and other reagents, so that the DpnI and PCR were compatible and would be carried out sequentially in a closed system.

Reaction conditions were modified for several purposes. These modifications resulted in improved results.

For example, reaction conditions were modified to eliminate the potential contamination by ~$10^8$ molecules of plasmid (1 ng of an 8 kbp plasmid) DNA in PCR vials. Use of DpnI to remove this contaminating plasmid DNA could not be achieved art an acceptable level under the manufacturer's recommended conditions (NEB, Beverly, Mass.). Under the modified conditions, DpnI cleaving efficiency was nearly 99%. Due to the exquisite sensitivity of PCR, the survival of even a few plasmid molecules ($10^6$) would generate a false positive signal. The buffer conditions were modified to ensure the removal of >99.999999% of the added $10^8$ molecules of plasmid, even in the presence of 1 µg genomic DNA.

In another modification in DpnI-PCR reaction, preincubation using DpnI is carried out prior to the PCR process. However, DpnI preparation from several manufacturers contained varying degrees of contamination by nucleases and proteases. These contaminants severely affected the PCR sensitivity.

Sensitivity of detection was reduced from <10 plasmid copies to >1000 copies. The nuclease resulted in loss of priming activity of the primers. The effect of nuclease contamination was overcome by the use of phosphorothorate oligonucleotides (primer) for PCR, heating the reaction at 60° C. for 10 minutes prior to incubation at 37° C. for DpnI digestion, or by pre-incubating the phosphorothorate oligonucleotide (primer) with single stranded DNA binding protein (SSB) prior to its addition into the reaction mixture.

Use of SSB in the reaction mixture also improved the specificity of PCR by decreasing the number of false priming events. The protease contamination effect which adversely affected PCR, presumably due to proteolytic inactivation of Taq polymerase, was overcome either by inclusion of gelatin at 0.02% in the PCR or by preheating the reaction for 10 minutes at 60° C. Inclusion of gelatin in the reaction restored the sensitivity of detection by PCR at ~10 copies of plasmid, even in the presence of 1 $\mu$g chromosomal DNA.

Inclusion of gelatin at 0.02% and SSB at 1 $\mu$g not only decreased the effect of protease and nuclease activities, but also increased the efficiency of PCR as determined by its sensitivity, and also reduced false priming by the oligonucleotide primers.

Furthermore, the preheating of the reaction mix at 60° C. for 10 minutes prior to DpnI digestion removed any contaminating enzymic activities that adversely affected the PCR process.

Below is the reaction buffer that is optimized for DpnI activity to remove nearly $10^8$ contaminating plasmid molecules for use of DpnI in the PCR reaction in a closed system, use of gelatin and SSB to inhibit protease and nuclease activities, respectively, in commercial DpnI preparation (also to increase PCR efficiency and decrease false priming, respectively), and by the use of a preheating step to eliminate the residual effects of contaminating activities inherent to commercial enzymes.

Choice of primer positions in DpnI-PCR is also selected in some embodiments as a means to increase performance of the assay. The primer positions have been chosen to span at least 3 DpnI sites. The reason for this is as follows. Dam methylase methylates at the $N^6$ position of adenines in a GATC sequence. However, in E. coli, KK strains containing a single copy of a wild-type dam methylase, a particular GATC sequence is methylated only in ~99% of the plasmid molecules. Therefore, if a primer was designed to span only one DpnI site, nearly 1% of the plasmid molecules would escape cleavage of DpnI and, therefore, be detectable by PCR and contribute to false positives. It was experimentally determined that PCR primers must span at least 3 GATC sites to ensure that at least 1 GATC site in $10^8$ plasmid molecules was methylated at the $N^6$ of adenines, and therefore be cleaved by DpnI. However, in strains containing either cloned copies of Dam genes, or with modified Dam methylase wherein the methylation of GATC sequence is nearly $10^8$ out of $10^8$ sites, primers may be designed to span just one GATC sequence.

Although a DpnI digestion to remove free bacterially-derived plasmid could be carried out around the time of the physical fractionation step, it is very important that a final DpnI digestion be carried out immediately before the PCR amplification, and under conditions that preclude any subsequent contamination that could result in false-positive PCR results. The closed-system DpnI PCR method of the invention increases the sensitivity of the integration assay by about two orders of magnitude. Since it is necessary to detect very small quantities of integrated plasmid sequences (in the range of 1–2 copies) in the presence of a relatively huge excess of genomic DNA, the PCR must be run so as to maximize sensitivity, PCR conditions that could easily result in false positive signals. The closed-system DpnI PCR method of the invention can detect approximately 100 copies of plasmid per mg of DNA, or one plasmid copy per $10^6$ genome equivalents (the genome equivalent is the quantity of genomic DNA found in one mammalian cell). This was demonstrated by creating a cell line which contained one single copy of integrated plasmid per genome. The closed-system DpnI PCR integration assay of the invention was capable of detecting integration at this level of sensitivity.

According to the present invention, the DNA from the sample is subjected to digestion by DpnI. All of the plasmid DNA not integrated into the eukaryotic chromosome is recognized and digested. However, no eukaryotic chromosomal DNA is digested. Nor is plasmid DNA integrated into the eukaryotic chromosomal DNA that has undergone repair or replication, processes known to alter the GATC adenine methylation pattern. Thus, the assay can be used to detect the presence of plasmid DNA integrated into the eukaryotic chromosomal DNA that has undergone repair or replication by selectively digesting non-integrated, non-repaired or non-replicated DNA.

The integrated plasmid DNA that has undergone repair and/or replication remains intact. Amplification protocols can be performed using primers that flank the DpnI sites in the plasmid DNA sequence. Accordingly, plasmid DNA will not be amplified if it has undergone DpnI digestion since the primers will hybridize to sites on either side of the site where the nucleic acid molecule is cleaved by DpnI and will therefore will not amplify DNA. If, however, the plasmid DNA has not been digested, the primers will hybridize to it and amplify the DNA sequence therebetween.

To practice the invention, the DNA of a sample that includes eukaryotic cells that have been exposed to plasmid DNA is first digested with one or more non-DpnI restriction enzymes that cleave the plasmid DNA. The restriction enzyme or enzymes is not DpnI. The restriction sites for this/these enzymes are not within the primer sequences or between the primer sequences of a set of primers, i.e., within the sequence to be amplified by a set of primers.

It is preferred that the DNA is fractionated after it is cleaved by the enzyme or enzymes which digest sequences within the plasmid DNA sequence. The digested DNA is fractionated according to any one or several well known fractionation methods such as size fractionation by column chromatography, size and charge fractionation by electrophoresis, density fractionation by centrifugation, or charge fractionation by CE (capillary electrophoresis).

After digestion by non-DpnI restriction enzyme (s) and fractionation, the DNA is digested with DpnI and plasmid sequences are amplified using primers that flank DpnI restriction sites.

EXAMPLE

Example 1

The DpnI PCR Method was developed to detect plasmid DNA and plasmid DNA sequences which have been integrated into chromosomal DNA of eukaryotic cells, in the presence of free (non-integrated) plasmid DNA. Specifically, the plasmid DNA sequences are produced in a strain of E. coli (dam+) containing deoxyadenosine methylase, and are therefore methylated in a specific pattern. The eukaryotic DNA is methylated in a different pattern.

After an i.m. injection of plasmid DNA into mammalian muscle, a mixture of free plasmid DNA and chromosomal DNA exists. In addition, integrated plasmid DNA might also be present as a very small proportion of this mixture. This integrated plasmid DNA could potentially arise from homologous or non-homologous recombination of plasmid, DNA into chromosomal DNA. This integration event, when repaired, or when the chromosome replicates, becomes a permanent addition to the chromosome, and the integrated plasmid sequence then loses the bacterial methylation pattern and incorporates the eukaryotic methylation pattern. This integrated sequence could then be detected by PCR.

However, the presence of free plasmid DNA (even a few copies) in the muscle would confound interpretation of the data, because it would be impossible by standard PCR to distinguish free versus integrated copies of the same plasmid. Therefore it was necessary to develop a method to selectively identify integrated plasmid sequences in the presence of the same plasmid existing in the free, non-integrated state.

To solve this problem, it was necessary to take advantage of a chemical difference between mammalian genomic DNA and E. coli (dam+) produced plasmid DNA. The deoxyadenosine methylase (Dam) of E. coli K12 strains is an unique enzyme that methylates adenine nucleotides when present as a GATC sequence. GATC methylation at the adenines is signatory to E. coli K12 DNA. Mammalian cells do not have a GATC sequence-dependent deoxyadenosine methylase activity. Furthermore, the restriction endonuclease DpnI is known to only recognize and cleave at GATC sequences with the E. coli K12 methylation pattern. Pre-treatment of DNA isolated from tissues with DpnI therefore effectively eliminates free plasmid sequences within a mixture of free plasmid and chromosome-integrated plasmid sequences. Upon elimination of free plasmid DNA in the mixture, it is possible to use the specificity and sensitivity of the PCR to analyze for plasmid DNA integrated at random sites within the chromosome.

PCR has been used as a routine method for amplifying and analyzing DNA of a specific sequence. However, in practice its overall ability of detecting small numbers of specific sequences has been limited due to its exquisite sensitivity. The "PCR contamination" problem is a well known phenomenon in the modern molecular biology laboratory. Increased sensitivity leads to numerous "false positives" in PCRs, due to in many cases a few molecules of "airborne" contaminating control DNAs. This severely limits the overall sensitivity of PCR to the "background" introduced from the laboratory, no matter what precautions are taken. This becomes a severe problem when employing PCR conditions for maximum signal sensitivity, such as for analyzing a single or a few integrated plasmid DNA sequences within an enormous excess of chromosomal DNA. However, this "false positive" problem was eliminated by using the new method described in herein termed "DpnI PCR".

DpnI PCR is quite simple. After chromosomal DNA is prepared, by any standard method, it is added to a standard PCR reaction mixture, with thermostable polymerase, primers, etc. At this point, DpnI (1–2 µL, 20–40 units) is also added to the PCR mixture. The tubes are closed (sealed) and the standard PCR is modified by programming two pre-incubation steps prior to standard thermocycling. The first step is at elevated temperature (60° C., 10 min) which removes contaminating nuclease activity in DpnI preps by heat inactivation. This step does not destroy DpnI activity. This step could be eliminated if phosphorothioate primers are used in the PCR. The second pre-incubation step (37° C., 60 min) allows for complete digestion and removal of adenine-methylated plasmid DNA. Standard PCR thermocycling is then carried out (on the same sealed tubes) for signal amplification. The signal in this case would be generated specifically from integrated plasmid DNA sequences, and not from free (non-integrated) plasmid.

The sensitivity of detection of integrated sequences is greatly enhanced (by about $10^3$ fold) by combining the DpnI PCR method with any method that fractionates chromosomal DNA (such as gel filtration, electrophoresis, gradient centrifugation). An example is provided herein using DpnI PCR with gel filtration chromatography to detect integrated plasmid sequences at very high sensitivity.

It should be noted that any DNA methylated specifically by the dam methylase will be digested by DpnI. Therefore, if the dam genes were cloned into other bacteria, yeast, insect cells, plant cells, mammalian cells, etc., it would act to specifically methylate DNA in the pattern of E. coli. Alternatively, the plasmid could be methylated using the dam enzyme in vitro. In fact, eukaryotic DNAs, episomal sequences, viruses, and viral vectors, as examples, could be prepared with this methylation pattern. They would then be subject to digestion with DpnI. The DpnI PCR method could then be used to amplify other DNAs (such as eukaryotic chromosomal) in the presence of these methylated DNAs. This might have utility for monitoring integration of other viruses and viral vectors. For example, adenovirus or herpesvirus vectors for gene therapy could be replicated and packaged in cells that contain the E. coli dam gene. These vectors could then be effectively monitored for integration into mammalian chromosomal DNA by the aforementioned methods.

Example 2
Generation of the Positive Control

A known amount of positive control DNA is mixed with known amounts of genomic DNA, prior to digestion by restriction enzymes other than DpnI. The positive control is the plasmid sequence not methylated on the adenines in the GATC sites, so that the plasmid sequence is not cleaved in the subsequent digestion step by DpnI in the DpnI-PCR. Non-methylated adenines in the GATC sites in the plasmid sequence can either be prepared by isolating plasmid DNA from dam⁻ mutants of E. coli, eg. JM110.

E. coli JM110 (rpsL thr leu thi1 lacY galK galT ara tonA tsx dam dcm supE44 Δ (lac proAB) (F' traD36 proAB lacI ZΔM15) was made competent, transformed with plasmid 95-03 DNA non-methylated at GATC sites was prepared from the E. coli strain JM110 (dam), by alkaline lysis plasmid isolation procedure described in (Sambrook et al., 1989 Molecular Cloning, A Laboratory Manual, Cold Spring Harbor Laboratory, Cold Spring Harbor N.Y.).

The unmethylated form of DNA (at the adenines in the GATC sites) can also be prepared by selecting a stably integrated cell line that contains a known defined number of plasmid integrants. An RD cell line (human rhabdomyosarcoma cell line), that was transfected with the plasmid which was previously engineered to contain a selectable marker such as an antibiotic resistance gene (hygromycin) has been used for this purpose. The cells were allowed to grow in the presence of hygromycin following transfection. When the cells reached confluency, single colonies were isolated by limiting dilution. These single colonies were built up to larger flask cultures, and the DNA was isolated. The DNA was characterized to contain the plasmid sequence by PCR using hygromycin specific primers. In order to select a cell line that contained a singular whole plasmid integrant, the DNA was digested with a set of restriction enzymes either singly or in combination, either using enzymes that digest within the plasmid of exclusively outside of the plasmid. The pattern of fragments detected in an autoradiogram when probed with labelled plasmid DNA will aid in the selection of a singular whole plasmid integrated cell line.

Evaluation of Assay

In order to evaluate the integration assay, it was necessary to create cell lines containing integrated 95-03 sequences. Twenty cell lines were initially chosen to be characterized by both Southern blot and PCR analyses in order to examine integration events. Once characterized, the cell lines were able to serve as reference standards for determining the amount of an integrated 95-03-derived sequence per genome equivalent.

Human rhabdomyosarcoma cells (RD2) were transfected with 95-03H DNA according to a modification of a calcium phosphate-mediated transfection procedure (Sambrook et al., 1989 Supra). The transfection mix was removed from cells 24 hours post-transfection, and cells were washed with phosphate buffered saline (PBS) and refed with media. At three days post-transfection, $2 \times 10^6$ cells were trypsinized and resuspended in 15 mL of media (200 mg/mL hygromycin) and seeded into a T75 flask. When the cells reached confluency, they were seeded into ten 96-well plates by limiting dilution in media containing hygromycin. Cells were visualized by phase contrast microscopy at 24 hours post seeding. Thirty wells were identified which contained single cells. These cells were monitored at 24 hours post seeding. Thirty wells were identified which contained single cells. These cells were monitored for up to two weeks, allowing for growth of single colonies in the wells. When cell colonies reached 20% to 25% confluency in a well, the cells were trypsinized and seeded into a six-well plate, and subsequently into a T75 flask and finally into three T150 flasks. When cells in the T150 flasks reached confluency, they were harvested, resuspended in 3 to 5 mL of 95% FCS/5% DMSO, and aliquotted into cryovials and placed at −70° C. The following day the cells were shifted to −135° C. for long term storage. At 3 to 7 days post freezing, one vial of each cell line was thawed, revived, and cultured for two weeks to monitor cell viability. Of the initial 30 clones identified, only 20 clones survived the final selection. Those clones were named RD-003H1 through RD-003H20. Analysis of the Cell Line DNA by Southern Blot:

The presence of integrated 95-03H sequences was first assayed by Southern blot analysis. Chromosomal DNA from the twenty RD-003H cell lines and the parental RD2 cell line was digested to completion with PvuII, subjected to agarose gel electrophoresis, transferred to nylon, and probed with [$^{32}$P]-labelled 95-03H DNA. PvuII cleaves twice within 95-03H DNA at map coordinates 5362 and 8307. PvuII digestion of free 95-03H plasmid DNA generates a 2.9 and 5.9 kbp fragment.

Southern Blot Analysis of RD and RD-003H cell lines (H2 to H9) were performed. The blot was prepared by transferring 10 μg of PuvII digested (overnight at 37° C.) DNA from stably transfected RD-003H (marked H2 to H9) cell lines and from RD2 cells (RD). The RD-003H3 cell line genomic DNA contained a single integrated copy of 95-03H, as determined by its pattern of bands after PvuII digestion. This cell line contained a single 5.9 kbp fragment, as well as smaller 3.0 and 1.0 kbp fragments. This result suggests that 95-03H DNA was linearized within the 2.9 kbp PvuII fragment and integrated within the chromosome. The additional 5.0 kbp band corresponds to non-specific hybridization with a band from the control RD2 cell line.

Detailed Southern Blot Analysis of RD-003H3 Cell Line DNA

Previous Southern blot analysis suggested that cell line RD-003H3 had a singular complete plasmid 95-03H integrated into the genomic sequences. Quantitation of stably-integrated 95-03H plasmid DNA sequences RD-003H3 chromosomal DNA was further carried out by a detailed Southern blot analysis. Chromosomal DNA from RD-003H3 cells and the parental RD cell line were digested to completion either singularly with BclI and PvuII or in combination, using BamHI, SmaI, and PvuII with BclI.

Fifteen (15) to 16 μg of RD-003H3 cell line DNA or RD cell line DNA were digested to completion with BclI, or BamHI and BclI, or SmaI and BclI, or PvuII and BclI, or PvuII, and electrophoresed on a 0.7% agarose gel. The DNA was transferred to Hybond N+ (Amersham, Inc., Chicago, Ill.), a nylon membrane. The blot was probed with $^{32}$P labelled 95-03H plasmid DNA (Multiprime, Amersham, Inc.).

BclI, a six base cutter, cleaves frequently within the chromosomal DNA from RD cells or from RD-003H3 cells, but does not cleave within 95-03H DNA sequences. RD-003H3 cell DNA digested with BclII yields a single hybridizable band when probed in a Southern blot with 95-03H sequences. This band migrates at a position just above the 12 kbp marker, and is specific for the RD-003H3 cell line as it does not appear in the lane containing BclI digested RD cell DNA. This result strongly suggests that 95-03H has inserted at one chromosomal locus in the cell line. This result does not rule out the possibility of more than a single copy of 95-03H having inserted in tandem at a single locus. However, the size of the BclI fragment (approximately 12 kbp) excludes the possibility of tandem integration involving more than two complete copies of the 8 kbp plasmid sequence.

A BamHI-BclI double digestion of RD-003H3 DNA contains two fragments that hybridize to the 95-03H probe. These fragment sizes are 12 kbp and 4 kbp respectively, and are not seen in DNA from the parental RD cell line. BamHI cleaves once within 95-03H DNA. A BamHI-BclI double digest of RD-003H3 DNA would therefore be expected to yield a maximum of two detectable bands if 95-03H has integrated as a single copy. If 95-03H has integrated as a dimer, a maximum of three hybridizable bands would occur. The results from this digest are therefore consistent with a single copy integration event.

A SmaI-BclI double digest hybridizes to the 95-03H probe DNA to give rise to a doublet band with an apparent mobility of about 7 kbp each. Since SmaI cleaves twice within 95-03H DNA, a SmaI-BclI digest would be expected to yield a maximum of three detectable bands if 95-03H has inserted as a dimer. The RD cell line DNA does not cross hybridize to the labelled probe. These results also are consistent with the presence of a single copy of 95-03H inserted into RD-003H3 DNA.

Double digestion of RD-003H3 DNA with PvuII and BclI yields three fragments that hybridize to the 95-03H probe, that are approximately 5 kbp, 4 kbp, and 2 kbp respectively and are specific for the RD-003H3 cell line. PvuII cleaves twice within 95-03H DNA. A PvuII-BclI double digestion of RD-003H3 DNA would therefore be expected to yield a maximum of three detectable bands if 95-03H is present as a single copy insertion. A maximum of five bands is expected if a dimer of 95-03H has inserted in tandem. These results confirm our contention of a single integrated copy of 95-03H plasmid in RD-003H3 cell line.

PvuII digestion of RD-003He DNA yields three fragments that contain 95-03H sequences. These fragments are approximately 5 kbp, 4 kbp, and 2.5 kbp. PvuII digestion of RD-003H3 is expected to yield a maximum of three detectable bands if 95-03H is present as a single copy and a maximum of five bands if 95-03H has inserted as a dimer. The results are once again in agreement with one copy of 95-03H sequence in the RD-003H3 cell line.

Southern blot analysis of the RD-003H3 cell line is consistent with 95-03H DNA integration at one chromosomal locus. The results also demonstrate that 95-03H is integrated as a single copy at this locus. The data support the conclusion that DNA from the RD-003H3 cell line is appropriate to use as a positive control for a single-copy insertion event in this integration assay.

Example 3
PCR Analysis of RD-003H3 Cell Line DNA

Cell line RD-003H3 was chosen for a detailed PCR analysis as it clearly contained one integrated sequence by Southern blot. A panel of PCR primer sets was designed such that the resulting PCR products would span the entire 95-03H plasmid. Any integrated 95-03H sequence could be identified using DpnI PCR with multiple primer sets. These primer sets span nearly 40% of the entire 95-03 plasmid sequence. The DpnI PCR analysis confirmed that the RD-003H3 cell line contained one 95-03H derived sequence, which mapped to nucleotide positions 274 to 8300 of the 95-03H plasmid. Sequences mapping between coordinates 301 to 273 of the circular plasmid could not be detected. This is consistent with the Southern blot result, indicating linearization occurred within the 2.9 kbp PvuII fragment, resulting in integration of the plasmid.

Example 4
Chromosomal DNA Isolation

Chromosomal DNA from cell lines and animal tissues were isolated by a modified phenol/chloroform extraction procedure as described below.

Isolation of DNA from RD2 Cells and RD-003H3 (95-03H Integrated RD2) Cells

Total genomic DNA was isolated from either control RD2 cells or from RD-003H3 cells. The tissue culture cells grown in hygromycin-containing media were incubated to confluence in T150 flasks. The cells ($10^7$) were harvested and frozen at $-70°$ C. until use. The cells were resuspended in 3 mL of 10 M Tris, 100 mM NaCl, 25 mM ethylenediaminetetraacetic acid [EDTA], pH 8.0, 0.5% sodium dodecylsulfate [SDS]). The chromosomal DNA was de-proteinized by a 3 hour digestion using proteinase-K (Worthington Biochemicals Corporation, Freehold, N.J.). Digestions were carried out initially at a proteinase-K concentration of 1 mg/mL, followed by 100 mg/mL additions of proteinase-K every 30 minutes at $55°$ C. in a waterbath to obtain a clear suspension. This was followed by three sequential extractions using phenol, phenol/chloroform, and chloroform, all in the presence of Phase-Lock-Light (5'-3', Inc., Boulder, Colo.). The aqueous phase was precipitated with ¼th volume of 10.0 M ammonium acetate and two volumes of ethanol, and the pelleted samples were air dried and dissolved overnight in TE (10 mM Tris, 1 mM EDTA; pH 8.0).

RNA was digested using 0.1 mg DNAse-free RNAse A (Worthington Biochemicals Corp.) for 30 minutes at $37°$ C. in a waterbath. The digested solution was extracted once with phenol/CHCl$_3$, followed by extraction with chloroform in the presence of Phase-Lock-Light, and reprecipitated in the presence of ¼ volume of 10.0 M ammonium acetate and two volumes of ethanol. The DNA pellet was washed with 70% ethanol, and was redissolved in a minimal volume of TE overnight at room temperature. The concentration of DNA in solution was determined by its absorbance at 260 nm.

Isolation of DNA from Rabbit Tissues

DNA was isolated from tissues of male and female rabbits 57 and 85 days following intramuscular injection with 400 mg of 95-03 vaccine formulation. Muscle, inguinal lymph nodes, spleen, ovaries, lungs, liver, and heart of the rabbit from the 85 day time point, and the muscle and lymph nodes of the rabbit from the 57 day time point were used to isolate the DNA reported in this study. The DNA concentrations were determined by their absorbance at 260 nm.

Frozen tissue samples were sliced into 1.6 to 6.0 g pieces, and were incubated at $65°$ C. in 10 mM Tris, 100 mM NaCl, 25 mM EDTA; pH 8.0, 0.5% SDS (5 mL/slice of tissue), for 3 hours in the presence of 1 mg/mL proteinase-K (Worthington Biochemicals Corp.) in a rocking platform in a hot air oven at $55°$ C. Proteinase-K additions were done as described above. The samples were phenol/chloroform extracted and RNAse treated as described above (Isolation of DNA from RD2 Cells and RD-003H3 [95-03H Integrated RD2] Cells).

Digestion and Sephacryl S-1000 Chromatography of Genomic DNA from Cells and Rabbit Tissues Genomic DNA (in 0.8 mL) was digested simultaneously with two restriction enzymes, 1,000 units of NruI and 2,000 units of SacI in the manufacturer-supplied NruI buffer (New England Biolabs, Beverly, Md.) in a total volume of 1.0 mL at $37°$ C. overnight. The samples were phenol/chloroform extracted and applied on the Sephacryl S-1000 column.

The positive control sample was generated as follows: genomic DNA (0.8 mL) was mixed with RD-003H3 cell line DNA (0.5 ng=78 copies), and was subjected to restriction digestion as described in the preceding section.

DNA gel filtration chromatography was performed on 84 mg to 762 mg of DNA, as indicated in table and FIGURE legends, isolated from various tissues. DNA was separated using a 30×1.6 cm Sephacryl S-1000 column (Pharmacia Biotech, Inc., Piscataway, N.J.) (bed volume of 75 mL), using either Tris-HCl; 100 mM, ammonium acetate; 2 M, 0.01% ethanol and EDTA; 0.1 mM (pH 8.0/HCl), or Phosphate buffered saline containing an additional 50 mM NaCl, and 0.01% SDS and 5% ethanol at a flow rate of 1 mL/minute. Two milliliter (2 mL) fractions were collected. The DNA in each fraction was precipitated using 1.6 mL of isopropanol (0.8 v/v), at $-20°$ for 15 minutes. The precipitate was centrifuged at 12,000 g for 15 minutes, and washed with 1 mL 70% ethanol, vacuum dried and resuspended in 0.1 mL of water.

Before each column, chromatographic procedure the column was washed with 75 mL of 1 N NaOH, and 1.6 column volume of elution buffer. The elution buffer and the NaOH solutions were filtered through 0.2 mm filters before use.

Selective Digestion Using DpnI

The effect of DpnI on Adenine Methylated and Unmethylated GATC Containing Sequences was evaluated. Rabbit genomic DNA (0.2 μg), 95-03 plasmid from *E. coli* strain DH10B (0.2 μg), 95-03 plasmid from *E. coli* strain JM110 (dam$^-$, 0.2 μg), rabbit genomic DNA (0.2 μg) pre-incubated at 37° C. overnight in the presence of 40 units of DpnI, 95-03 plasmid from *E. coli* strain DH10B (0.2 μg) pre-incubated at 37° C. overnight in the presence of 40 units of DpnI, 95-03 plasmid from *E. coli* strain JM110 (dam⁻, 0.2 μg) pre-incubated at 37° C. overnight in the presence of 40 units of DpnI, rabbit genomic DNA (0.2 μg) digested overnight with 10 units of BclI were compared by gel electrophoresis. DpnI does not digest chromosomal DNA, despite several hours of over-digestion with four times more DpnI than recommended by the manufacturer. Similarly, DpnI did not digest non-methylated plasmid sequences when derived from the dam strain of *E. coli*, JM110.

To demonstrate that adenine in GATC Sequences is not methylated in eukaryotic DNA, DpnII was used. 2 μg of rabbit genomic DNA digested with 20 units of DpnII and compared by electrophoresis to 2 μg rabbit genomic DNA incubated with 20 units of DpnI. Digestions were carried out overnight at 37° C. Results demonstrate that adenines in genomic DNA are not methylated at GATC sequences as evidenced by the DpnII mediated digestion of rabbit skeletal muscle DNA. DpnII cleaves only GATC sequences when they are methylated.

Optimization of DpnI Digestion

Efficiency of DpnI Digestion of DH10B Cloned 95-03 Sequences in the Presence of Genomic DNA was evaluated. Ten micrograms (10 μg) of rabbit genomic DNA isolated from skeletal muscle tissue and 1 μg 95-03 plasmid DNA were digested with varying amounts of DpnI at 37° C., either singly or in a mixture having 0.2 μg chromosomal DNA and 1 μg 95-03 plasmid DNA. Genomic DNA from rabbit skeletal muscle is not digested by DpnI plasmid DNA is completely digested by DpnI in the presence or absence of muscle genomic DNA. DpnI digestion of DH10B-derived plasmid sequences is complete when chromosomal DNA up to 10 μg was added to the reaction mix. These results indicate that DpnI is able to digest free plasmid sequences to completion in the presence of excess chromosomal DNA.

Polymerase Chain Reaction (PCR)

The S-1000 fractions following resuspensions in water was used in the PCR. Fifteen to 60 microliters of the sample was used in the reaction.

A typical PCR buffer contained components supplied by the manufacturer (Perkin Elmer/Applied Bioscience, Foster City, Calif.), and 10 units of thermostable AmpliTaq DNA polymerase, 0.02% PCR grade gelatin (U.S. Biochemicals, Cleveland, Ohio), 1 μg of PCR grade single stranded DNA binding protein (U.S. Biochemicals), 0.2 mM of each of the dNTPs (Perkin Elmer/Applied Biosciences), 80 pmoles of primers (Research Genetics, Huntsville, Ala.) (FIG. 10), 1 mM DTT (Sigma Chemical Corporation), and 40 units DpnI (2 uL) (NEB, Beverly, Mass.). The thermocycler was programmed for DpnI digestions to include the 60° C. (10 minutes) and 37° C. (60 minutes) pre-incubation steps prior to the 40 PCR cycles. The mixture was taken through temperature cycles for the DpnI predigestion and the PCR process using the 9600 PCR thermocycler (Perkin Elmer/Applied Biosystems). The sequence of the temperature shifts following the initial singular incubations at 60° C. for 10 minutes, and 37° C. for 60 minutes were as follows: 94° C. (1 minute), 55° C. (2 minutes), 72° C. (3 minutes). The sequence was repeated 40 cycles.

Experiments were preformed to determine if DpnI selectively digests free plasmid but not integrated plasmid sequences using a DpnI digestion coupled with a PCR Assay. Two samples of RD cell line DNA (2.8 μg), RD-003H3 cell line DNA (1.95 μg), RD-003H12 cell line DNA (1.35 μg), RD-003H15 cell line DNA (1.27 μg), and 95-03H plasmid DNA from DH10B (2 ng) were pre-incubated in the presence or absence of DpnI (20 units). DpnI did not digest chromosomal DNA, and did not digest integrated plasmid sequences in chromosomal DNA, from the RD-003H3 cell lines, as determined by PCR. At high PCR sensitivities with an ability to detect <5 copies, airborne or otherwise introduced contamination of plasmid sequences can affect the outcome of the PCR result. This was overcome by including DpnI in the PCR buffer. At 37° C. pre-incubation prior to the PCR cycle allows for efficient removal of contaminating bacterially derived sequences. Inclusion of a DpnI (20 units) digestion step at 37° C. for one hour prior to the PCR process can effectively eliminate 10 ng ($10^9$ copies) of added bacterially-derived 95-03 sequences.

A primer set that flank several DpnI sites within 95-03H sequences in RD-003H cell lines were used in a PCR in the presence or in the absence of DpnI. Decreased intensity of signal in the presence of DpnI was due to the removal of methylated, free plasmid sequences. Control using a primer set that does not flank DpnI restriction sites showed no detectable effect of DpnI on the PCR. These results show that specific PCR signals are reduced due to digestion of free plasmid, rather than due to an effect of DpnI on PCR efficiency. These results indicate that the DpnI PCR methodology described can effectively detect DNA sequences at high sensitivity because of the elimination of "false positive" signals due to background plasmid contamination. No effect of DpnI on the PCR process was demonstrated using specific primers for 95-03H sequences in the RD-003H cell lines. The results indicate that the presence of DpnI in the PCRs do not effect the overall efficiency of the PCR.

To test whether DpnI affects PCR efficiency, several PCRs were carried out in the presence (20 units) and in the absence of DpnI with 2 μg ($3 \times 10^5$ genome equivalents) of RD-003H3 DNA. A set of reactions consisting of one DpnI containing and one without DpnI were withdrawn at various cycles of a 39 cycle PCR program. This primer set used primed within the hygromycin cassette in 95-03H and RD-003H3 sequences to give 362 bp product, and contain no DpnI sites between the primer binding sequences (DpnI insensitive). No detectable effect of DpnI enzyme was noticed on the PCR process. The sensitivity of the assay remained unchanged when DpnI was added to the reaction containing methylation-deficient DNA (either plasmid DNA derived from the dam strain of the *E. Coli*, JM110, or chromosomal DNA derived from skeletal muscle tissue). PCR amplification of RD-003H3 DNA using DpnI insensitive primer in the hygromycin cassette was not affected (18 to 39 cycles) by the inclusion of DpnI in the PCR.

PCR of Sephacryl S-1000 Fractions

Precipitated column fractions were redissolved in 100 μL of water. A 15 μL aliquot from each column fraction was analyzed by PCR. Each PCR was analyzed on a 1.5% agarose gel (FMC BioProducts, Rockland, Md.) containing 0.0025% ethidium bromide (EtBr) (Sigma Chemical Colo.), and electrophoresis was carried out in Tris-borate, EDT buffer at 120 mV.

Example 5

One milligram (1.0 mg) of rabbit skeletal muscle DNA was digested with NruI and SacI. One milliliter (1.0 mL) at 1 mg/mL was applied on the column and eluted at 1 mL/minute. In order to achieve the high PCR sensitives that are required to detect a plasmid DNA integration event that occurs infrequently in a large excess of genomic DNA, new methodology was developed based upon DNA size fractionation. This methodology eliminated the need to use much higher concentrations of genomic DNA in the PCRs, allowing the use of optimal conditions established using 1 to 3 mg of genomic DNA. These conditions allow detection of <10 copies of RD-003H3 sequences spiked into 3 mg skeletal muscle DNA. In the presence of higher concentrations of genomic DNA (10 mg in a PCR containing RD-003H3 cell line DNA as the spike), the PCR-based detection assay was greatly affected. Under these conditions, a 1,000 copy RD-003H3 DNA spike could not be detected. Therefore, the following strategy was developed to evaluate large amounts (up to milligram quantities) of chromosomal DNA sequences without significantly affecting the sensitivity of the PCR-based assay. Chromosomal DNA sequences are digested with two 6 bp-recognizing restriction enzymes (NruI and SacI) into small fragments, with a majority of the fragments larger than 40 kbp. This distribution is non-random and is due to the GC-rich recognition sequences of these enzymes. The same restriction enzymes would digest free and integrated plasmid sequences into much smaller fragments, since there are five NruI and SacI restriction sites present on the 95-03 plasmid. The plasmid sequences would be separated from the bulk of the chromosomal DNA on a Sephacryl size exclusion chromatogram. Integrated, plasmid-derived sequences in the presence of highly decreased amounts of chromosomal DNA could then be detected in column fractions by DpnI PCR.

Agarose Gel Electrophoresis of Column Fractions

One fifth of the S-1000 column fractions (2.0 mL) of a HincII digested plasmid (1 µg) and HincII digested genomic DNA (1 mg) were precipitated and redissolved. In TE, and were electrophoresed in 1% agarose in TBE buffer. Because chromatography is carried out on a large quantity of DNA, and because all plasmid sequence are forced into a few fractions with over a 1,000 fold decrease in chromosomal DNA content, high detection sensitivity of DpnI PCR is achieved. In fact, 50 to 100 copies of RD-003H3 derived integrated plasmid sequences spiked into 0.1 to 1 mg of chromosomal DNA ($1.5 \times 10^5$ to $1.5 \times 10^5$ genome equivalents) can be easily detected by this method. Consistent with this strategy, the specific Sephacryl S-1000 column fractions that contained plasmid-derived sequences are separated from over 99% of the total genomic DNA applied on the column. Nearly 4 mg genomic ($6 \times 10^8$ genomic equivalents) DNA spiked with either 78 or 780 genomic equivalents of RD-003H3 sequences elute in three fractions that contain less than 200 ng total DNA.

What is claimed is:

1. A method of detecting the presence of a foreign DNA sequence integrated in a chromosomal DNA molecule of a eukaryotic cell in a sample that contains chromosomal DNA molecules of eukaryotic cells and non-integrated foreign DNA, said method comprising the steps of:
a) digesting the DNA molecules of said sample with one or more restriction enzymes that cleave chromosomal DNA, foreign DNA sequences integrated in said chromosomal DNA molecules and non-integrated foreign DNA to produce DNA digestion segments,
wherein said eukaryotic cells are free of deoxyadenosine methyltransferase, said foreign DNA sequence contains at least one DpnI site, and said non-integrated foreign DNA molecules are produced in cells that contain deoxyadenosine methyltransferase;
b) fractionating said DNA digestion segments of a) to produce a plurality of fractions of DNA digestion segments containing chromosomal DNA and non-integrated foreign DNA;
c) forming a reaction mixture comprising (i) a fraction of (b) containing DNA digestion segments and (ii) restriction enzyme DpnI in PCR buffer containing DTT;
d) heating the reaction mixture to remove functional nuclease and protease contamination without inactivating DpnI;
e) digesting said DNA digestion segments with restriction enzyme DpnI in the reaction mixture, whereby non-integrated DNA is digested and integrated DNA remains undigested;
f) amplifying fragments of said integrated foreign DNA molecules using said DNA digestion segments of e) and sets of primers that flank said DpnI site in said foreign DNA molecules in conditions free of functional nuclease and protease activity; and,
g) detecting the presence of fragments of said foreign DNA molecules amplified in step f), wherein the presence of said amplified fragments indicates the presence of a foreign DNA sequence integrated into eukaryotic chromosomal DNA of eukaryotic cells.

2. The method of claim 1 wherein said foreign DNA molecules are plasmid DNA molecules.

3. The method of claim 2 wherein said plasmid DNA molecules are produced in an *E. coli* K12 strain.

4. The method of claim 3 wherein said plasmid DNA molecules are produced in *E. coli* K12 strain DH10B.

5. The method of claim 2 wherein said chromosomal DNA molecules of eukaryotic cells and non-integrated foreign DNA molecules of said sample are digested with one or more restriction enzymes that cleave foreign DNA sequences integrated in said chromosomal DNA molecules and in non-integrated foreign DNA selected from the group consisting of: NruI, SacI, Not1, Pac1, St1, Smu1 and SalI.

6. The method of claim 1 wherein said DNA digestion segments are fractionated by a fractionation protocol selected from the group consisting of: gel filtration, capillary electrophoresis, anion exchange chromatography, reverse phase chromatography, ion pair chromatography, and sucrose gradient methods.

7. The method of claim 5 wherein said fractionation of said DNA digestion segments is performed by gel filtration column chromatography.

8. The method of claim 2 wherein said digestion of said plasmid DNA with restriction enzyme DpnI and said amplification of fragments of said plasmid DNA using sets of primers that flank DpnI restriction enzyme sites in said plasmid DNA are performed consecutively in a closed container.

9. The method of claim 8 wherein said plasmid DNA molecules are produced in an *E. coli* K12 strain.

10. The method of claim 9 wherein said DNA digestion segments are fractionated by a fractionation protocol selected from the group consisting of: gel filtration, capillary electrophoresis, anion exchange chromatography, reverse phase chromatography, ion pair chromatography, and sucrose gradient methods.

11. The method of claim 10 wherein said chromosomal DNA molecules of eukaryotic cells and non-integrated plasmid DNA molecules of said sample are digested with one or more restriction enzymes that cleave plasmid DNA sequences integrated in said chromosomal DNA molecules and in plasmid DNA selected from the group consisting of: NruI, SacI, Not1, Pac1, St1, Smu1 and Sal1.

12. The method of claim 1 wherein said sample that contains DNA from eukaryotic cells is produced by:

i) harvesting eukaryotic cells;

ii) lysing harvested cells; and, iii) contacting lysed cells with one or more proteases.

13. The method of claim 12 wherein said eukaryotic cells are mammalian cells.

14. The method of claim 1, wherein said steps e and f are performed in a closed container.

15. The method of claim 1 wherein said primers are phosphorothioate oligonucleotide primers.

16. The method of claim 1 wherein gelatin and single stranded binding protein are used in reactions of said steps e and f.

17. The method of claim 1 wherein said heating is performed at 60° C. for about 10 minutes prior to DpnI digestion.

18. The method of claim 8 wherein said sample that contains DNA from eukaryotic cells is produced by:

i) harvesting eukaryotic cells;

ii) lysing harvested cells; and, iii) contacting lysed cells with one or more proteases.

19. The method of claim 18 wherein said eukaryotic cells are mammalian cells.

20. The method of claim 8 wherein said primers are phosphorothioate oligonucleotide primers.

21. The method of claim 8 wherein gelatin and single stranded binding protein are used in reactions of said steps e and f.

22. The method of claim 8 wherein said heating is performed at 60° C. for about 10 minutes prior to DpnI digestion.

23. A method for detecting the integration of foreign DNA into the chromosome of a eukaryotic cell which lacks deoxyadenosine methyltransferase, said method comprising the steps of:

(a) providing a sample that contains chromosomal DNA from a eukaryotic cell which lacks deoxyadenosine methyltransferase, wherein said sample further contains foreign DNA which contains methylated GATC sequences when non-integrated into chromosomal DNA and which contains unmethylated GATC sequences when integrated into chromosomal DNA, (b) digesting the chromosomal and foreign DNA in the sample with one or more restriction enzymes that cleave the chromosomal and foreign DNA without regard to methylation of the GATC sequences;

(c) fractionating the digested DNA of (b) to produce a plurality of fractions of DNA digestion segments containing chromosomal and foreign DNA;

(d) forming a reaction mixture comprising (i) a fraction of (c) containing DNA digestion segments and (ii) a restriction enzyme specific for methylated GATC sequences in PCR buffer containing DTT, (e) treating the reaction mixture to remove functional nuclease and protease contamination without inactivating the restriction enzyme specific for methylated GATC sequences;

(f) digesting the non-integrated foreign DNA in the reaction mixture, thereby leaving any integrated foreign DNA uncleaved by the restriction enzyme specific for methylated GATC sequences;

(g) subjecting the DNA digestion segments of (f) to DNA amplification using sets of primers which flank GATC sequences and which are specific to the foreign DNA, wherein the amplification is performed in the absence of functional nucleases and proteases, whereby integrated foreign DNA is amplified and non-integrated foreign DNA is not amplified; and (h) detecting the presence of amplified foreign DNA, wherein the presence of amplified foreign DNA indicates integration of the foreign DNA into the chromosome of the eukaryotic cell.

24. The method according to claim 23, wherein said reaction mixture comprises DpnI in a buffer that contains 5 mM DTT.

25. The method according to claim 24, wherein the treating step comprises heating DpnI to about 60° C. for about 10 minutes prior to step f.

26. The method according to claim 23, wherein the primers of step (g) are phosphorothioate oligonucleotide primers.

27. The method according to claim 26, wherein the phosphorothioate oligonucleotides are pre-incubated with single-stranded binding protein.

28. A method for detecting integration of plasmid DNA into the chromosome of a eukaryotic cell which lacks deoxyadenosine methyltransferase, said method comprising the steps of:

(a) providing a sample that contains chromosomal DNA from a eukaryotic cell which lacks deoxyadenosine methyltransferase, wherein said sample further contains foreign plasmid DNA which contains methylated GATC sequences when non-integrated into chromosomal DNA and which contains unmethylated GATC sequences when integrated into chromosomal DNA, (b) digesting the chromosomal and plasmid DNA in the sample with one or more restriction enzymes that cleave the chromosomal and plasmid DNA without regard to methylation of the GATC sequences;

(c) fractionating the digested chromosomal and plasmid DNA of (b) to produce a plurality of fractions containing DNA digestion segments;

(d) heating a reaction mixture comprising a fraction of (c) and restriction enzyme DpnI in PCR buffer containing 1 mM DTT at about 60° C. for about 10 minutes without inactivating DpnI;

(e) digesting said plurality of DNA digestion segments with restriction enzyme DpnI in said reaction mixture in the presence of gelatin and single-stranded binding protein, whereby non-integrated plasmid DNA is digested by DpnI and integrated plasmid DNA remains undigested by DpnI;

(f) subjecting the DNA digestion segments of (e) to DNA amplification using sets of primers which flank GATC sequences and which are specific to the plasmid DNA, whereby integrated plasmid DNA is amplified and the digested, non-integrated plasmid DNA is not amplified; and (g) detecting the presence of amplified plasmid DNA, wherein the presence of the amplified fragments indicate the presence of plasmid DNA integrated into the chromosome of the eukaryotic cell.

29. The method according to claim 28, wherein the restriction enzymes which cleave both integrated and non-integrated plasmid DNA comprise NruI and SacI.

30. The method according to claim 28, wherein the plasmid DNA contains three or more DpnI sites prior to integration.

31. The method according to claim 28, wherein the primer spans at least three GATC sites.

32. The method according to claim 28, wherein the primers are between 10 to about 200 nucleotides in length.

33. The method according to claim 32, wherein said primer is about 30 nucleotides in length.

34. A method for detecting the integration of foreign DNA into the chromosome of a eukaryotic cell which lacks deoxyadenosine methyltransferase, said method consisting of the steps:
  (a) providing a sample that contains chromosomal DNA from a eukaryotic cell which lacks deoxyadenosine methyltransferase, wherein said sample further contains foreign DNA which contains methylated GATC sequences when non-integrated into chromosomal DNA and which contains unmethylated GATC sequences when integrated into chromosomal DNA,
  (b) digesting the chromosomal and foreign DNA in the sample with one or more restriction enzymes that cleave the chromosomal and foreign DNA without regard to methylation of the GATC sequences;
  (c) fractionating the digested DNA of (b) to produce a plurality of fractions containing DNA digestion segments;
  (d) forming a reaction mixture comprising (i) a fraction of (c) containing DNA digestion segments, (ii) DpnI, and (iii) a PCR buffer containing 1 mM DTT;
  (e) heating the reaction mixture to about 60° C. for about 10 minutes, thereby removing functional nuclease and protease activity without inactivating DpnI;
  (f) incubating the reaction mixture with DpnI in the presence of gelatin and single stranded binding protein, thereby permitting digestion of non-integrated foreign DNA;
  (g) subjecting the DNA digestion segments of (f) to DNA amplification using sets of primers which flank GATC sequences and which are specific to the foreign DNA, wherein the amplification is performed in the absence of functional nucleases and proteases, whereby integrated foreign DNA is amplified and non-integrated foreign DNA is not amplified; and
  (h) detecting the presence of amplified foreign DNA, wherein the presence of amplified foreign DNA indicates integration of the foreign DNA into the chromosome of the eukaryotic cell.

35. The method according to claim 1, wherein the primers of step (g) span at least three DpnI sites.

36. The method according to claim 15, further comprising the step of pre-incubating the phosphorothioate oligonucleotide primer with single stranded DNA binding protein prior to its addition to the reaction mixture.

37. The method according to claim 23, wherein the primers of step (g) span at least three methylated GATC sites.

38. The method according to claim 28, wherein the primers of step (g) span at least three DpnI sites.

39. The method according to claim 34, wherein the primers of step (g) span at least three DpnI sites.

40. The method according to claim 1, wherein said reaction mixture comprises DpnI in a buffer that contains 1 mM DTT.

41. The method according to claim 23, wherein said reaction mixture comprises DpnI in a buffer that contains 1 mM DTT.

42. The method according to claim 28, wherein said reaction mixture comprises DpnI in a buffer that contains 5 mM DTT.

43. The method according to claim 34, wherein said reaction mixture comprises DpnI in a buffer that contains 5 mM DTT.

44. A method for detecting the integration of foreign DNA into the chromosome of a eukaryotic cell which lacks deoxyadenosine methyltransferase, said method comprising the steps of:
  (a) providing a sample that contains chromosomal DNA from a eukaryotic cell which lacks deoxyadenosine methyltransferase, wherein said sample further contains foreign DNA which contains methylated GATC sequences when non-integrated into chromosomal DNA and which contains unmethylated GATC sequences when integrated into chromosomal DNA,
  b) digesting the chromosomal and foreign DNA in the sample with one or more restriction enzymes that cleave the chromosomal and foreign DNA without regard to methylation of the GATC sequences;
  (c) fractionating the digested DNA of (b) to produce a plurality of fractions of DNA digestion segments containing chromosomal and foreign DNA;
  (d) forming a reaction mixture comprising (i) a fraction of (c) containing DNA digestion segments and (ii) a restriction enzyme specific for methylated GATC sequences in PCR buffer containing DTT, p1 (e) treating the reaction mixture to decrease nuclease and protease inhibition of PCR amplification without inactivating the restriction enzyme specific for methylated GATC sequences;
  (f) digesting the non-integrated foreign DNA in the reaction mixture, thereby leaving any integrated foreign DNA uncleaved by the restriction enzyme specific for methylated GATC sequences;
  (g) subjecting the DNA digestion segments of (f) to DNA amplification using sets of primers which flank GATC sequences and which are specific to the foreign DNA, wherein the amplification is performed in the absence of functional nucleases and proteases, whereby integrated foreign DNA is amplified and non-integrated foreign DNA is not amplified; and
  (h) detecting the presence of amplified foreign DNA, wherein the presence of amplified foreign DNA indicates integration of the foreign DNA into the chromosome of the eukaryotic cell.

45. The method according to claim 44, wherein said treating step comprises adding gelatin to the reaction mixture.

46. The method according to claim 45, wherein said treating step farther comprising adding single-stranded DNA binding protein to the reaction mixture.

47. The method according to claim 45, wherein said treating step comprises adding single stranded DNA binding protein to the reaction mixture.

48. The method according to claim 45, wherein said treating step comprises adding phosphorothioate oligonucleotide primers to the reaction mixture.

49. The method according to claim 48, wherein said treating step further comprises adding gelatin to the reaction mixture.

* * * * *

UNITED STATES PATENT AND TRADEMARK OFFICE
CERTIFICATE OF CORRECTION

PATENT NO. : 6,168,918 B1
DATED : January 2, 2001
INVENTOR(S) : C. Satishchandran It is certified that error appears in the above-identified patent and that said Letters Patent is hereby corrected as shown below:

Column 5,
Line 42, insert -- so -- between "dam"⁻ and "that".
Line 46, replace "dam-" with -- dam⁻ --.
Line 47, replace "dam-" with -- dam⁻ --.

Column 6,
Line 27, delete "the";

Column 7,
Line 26, "dam⁻ cells." replace with -- dam+ cells. --.

Column 10,
Line 59, "art" replace with -- at --.

Column 17,
Line 47, "cells" replace with -- cells: --.

Column 18,
Line 58, delete ",".

Column 20,
Line 55, "(Sigma Chemical Colo.)" replace with -- (Sigma Chemical Co.) --.

UNITED STATES PATENT AND TRADEMARK OFFICE
CERTIFICATE OF CORRECTION

PATENT NO. : 6,168,918 B1
DATED : January 2, 2001
INVENTOR(S) : C. Satishchandran It is certified that error appears in the above-identified patent and that said Letters Patent is hereby corrected as shown below:

Column 26,
Line 27, delete "p1" and start a new line with (e) treating the reaction mixture to decrease nuclease and protease inhibition of PCR amplification without inactivating the restruction enzyme specific for methylated GATC sequences;

Signed and Sealed this

Thirteenth Day of November, 2001

Attest:

NICHOLAS P. GODICI
Attesting Officer    Acting Director of the United States Patent and Trademark Office